US011998717B2

(12) United States Patent
Tada

(10) Patent No.: US 11,998,717 B2
(45) Date of Patent: Jun. 4, 2024

(54) PIEZOELECTRIC MOTOR AND INJECTION DEVICE

(71) Applicant: Piezo Sonic Corporation., Tokyo (JP)

(72) Inventor: Kouhei Tada, Tokyo (JP)

(73) Assignee: Piezo Sonic Corporation., Tokyo (JP)

( * ) Notice: Subject to any disclaimer, the term of this patent is extended or adjusted under 35 U.S.C. 154(b) by 727 days.

(21) Appl. No.: 17/266,310

(22) PCT Filed: Aug. 2, 2019

(86) PCT No.: PCT/JP2019/030568
§ 371 (c)(1),
(2) Date: Feb. 5, 2021

(87) PCT Pub. No.: WO2020/031910
PCT Pub. Date: Feb. 13, 2020

(65) Prior Publication Data
US 2021/0299349 A1 Sep. 30, 2021

(30) Foreign Application Priority Data
Aug. 10, 2018 (JP) .................................. 2018-151666

(51) Int. Cl.
*A61M 5/00* (2006.01)
*A61M 5/20* (2006.01)
(Continued)

(52) U.S. Cl.
CPC .............. *A61M 5/007* (2013.01); *A61M 5/20* (2013.01); *H02N 2/103* (2013.01); *H02N 2/126* (2013.01);
(Continued)

(58) Field of Classification Search
CPC ........ H02N 2/103; H02N 2/126; H02N 2/145; A61M 5/007; A61M 5/20; A61M 5/31596;
(Continued)

(56) References Cited

U.S. PATENT DOCUMENTS

| 5,313,132 A | 5/1994 | Nakanishi |
| 5,352,950 A | 10/1994 | Shirasaki |
| 2015/0229240 A1* | 8/2015 | Wischnewskiy ....... H02N 2/103 310/317 |

FOREIGN PATENT DOCUMENTS

| JP | 03-018280 A | 1/1991 |
| JP | 03-285573 A | 12/1991 |

(Continued)

OTHER PUBLICATIONS

International Search Report dated Oct. 21, 2019 for the corresponding International Patent Application No. PCT/JP2019/030568.

*Primary Examiner* — Emily P Pham
(74) *Attorney, Agent, or Firm* — Leason Ellis LLP; Melvin C. Garner; Mitsuhiro Haraguchi

(57) ABSTRACT

A piezoelectric motor includes: a stator having an elastic body, a piezoelectric element and a sliding member adhesively attached to the elastic body; a rotor having an annular member, which includes a disc spring portion and a basic body portion in contact with the sliding member, and a fixture portion to which the annular member is fixed; and a shaft that rotates with the rotor, wherein the disc spring portion of the annular member is fixed to the fixture portion which is fixed to the shaft.

15 Claims, 8 Drawing Sheets

(51) Int. Cl.
*H02N 2/10* (2006.01)
*H02N 2/12* (2006.01)
*H02N 2/14* (2006.01)
*F16H 25/20* (2006.01)
*F16H 25/22* (2006.01)

(52) U.S. Cl.
CPC ..... *H02N 2/145* (2013.01); *A61M 2205/0294* (2013.01); *A61M 2205/103* (2013.01); *F16H 2025/2081* (2013.01); *F16H 25/2204* (2013.01)

(58) Field of Classification Search
CPC ..... A61M 2205/0294; A61M 2205/103; F16H 25/2204; F16H 2025/2081
See application file for complete search history.

(56) References Cited

FOREIGN PATENT DOCUMENTS

| | | |
|---|---|---|
| JP | 04-017583 A | 1/1992 |
| JP | 0491672 A | 3/1992 |
| JP | 04-344181 A | 11/1992 |
| JP | 08280184 A | 10/1996 |
| JP | 10-042578 A | 2/1998 |
| JP | 10-191666 A | 7/1998 |
| JP | 2001-016875 A | 1/2001 |
| JP | 2003253073 A | 9/2003 |
| JP | 2009077603 A | 4/2009 |
| JP | 2012-191846 A | 10/2012 |
| JP | 2013-005712 A | 1/2013 |
| JP | 2018-002774 A | 1/2018 |
| JP | 2018-099002 A | 6/2018 |
| JP | 6829916 B2 | 1/2021 |

\* cited by examiner

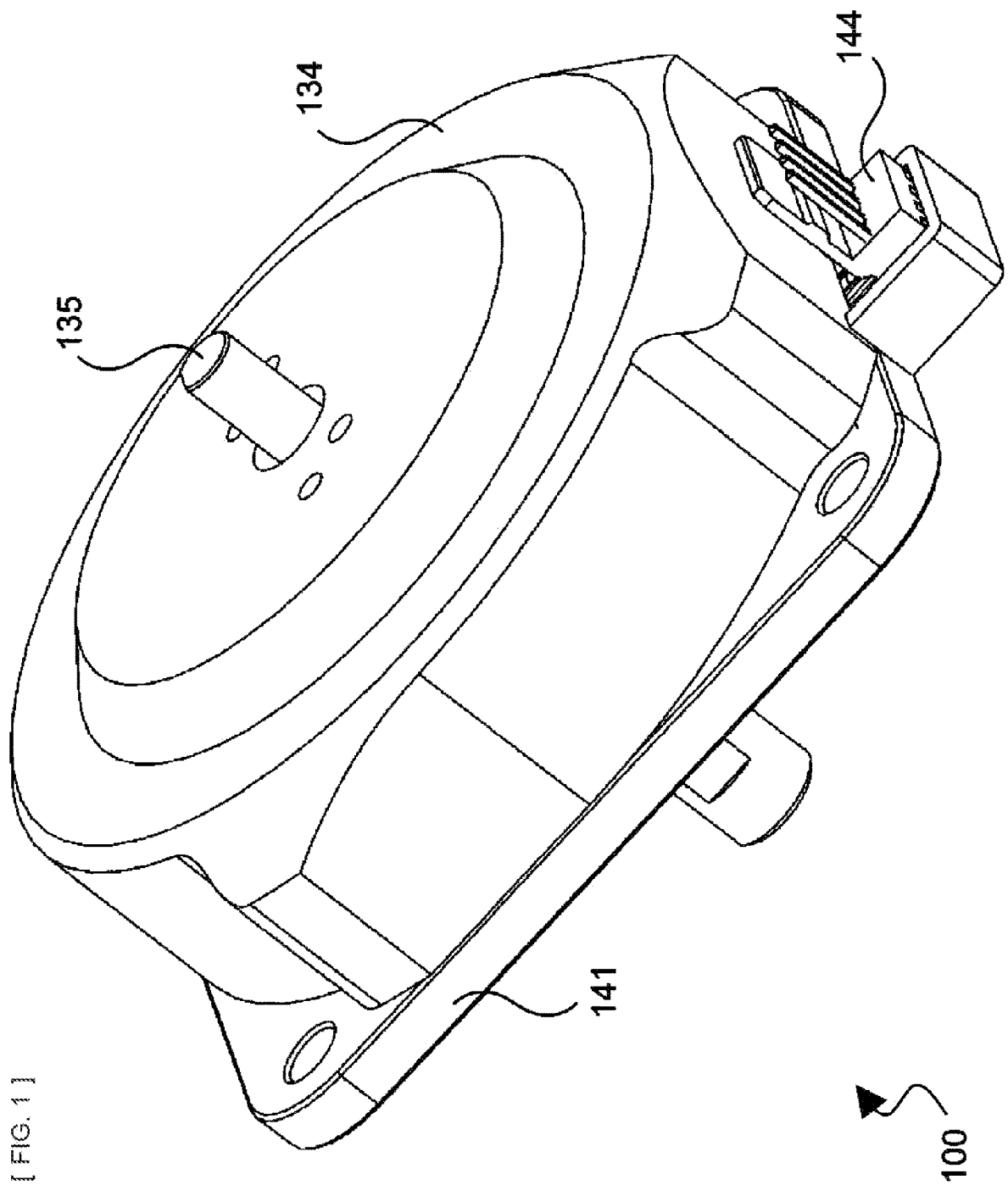
[FIG. 1]

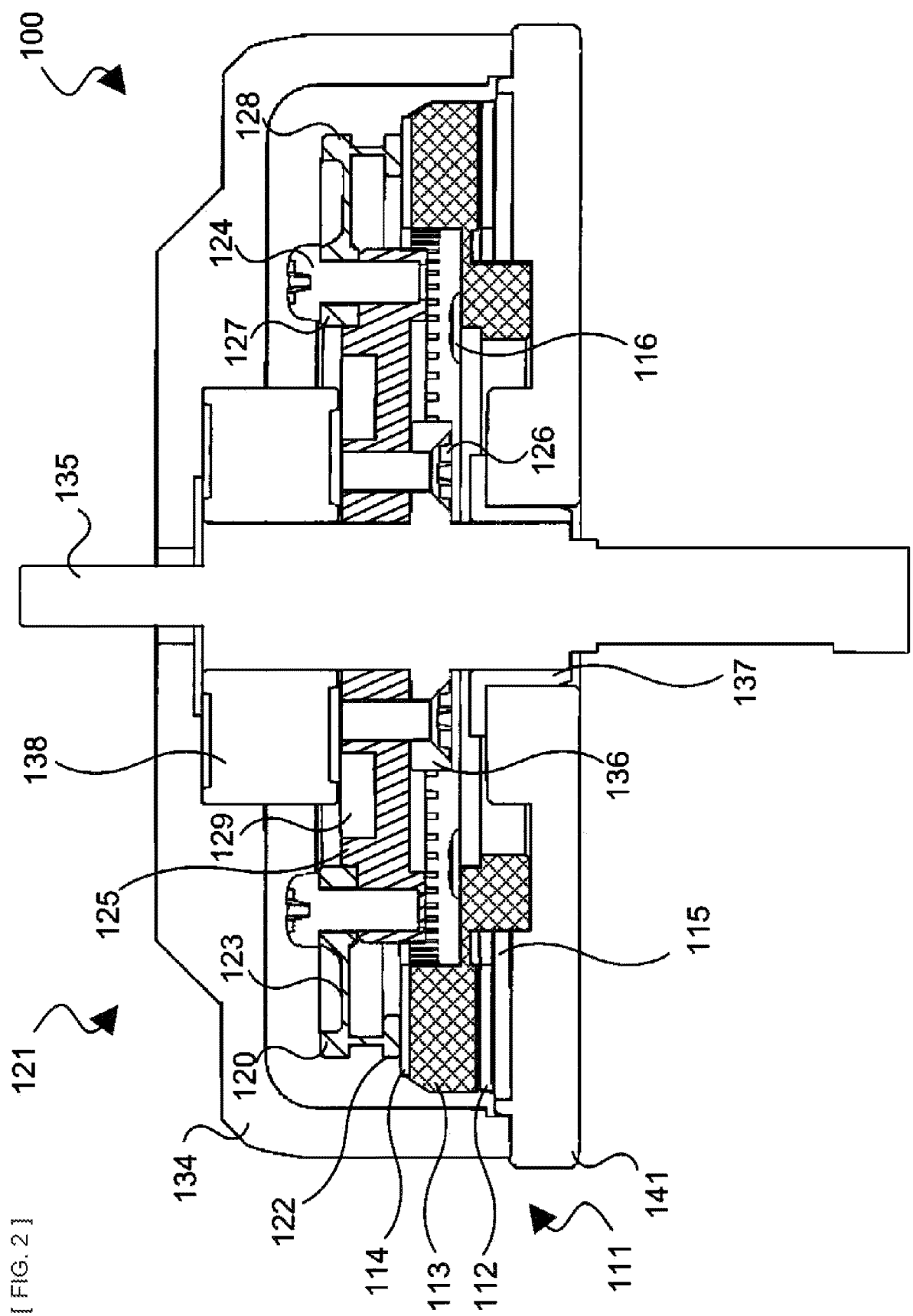
[FIG. 2]

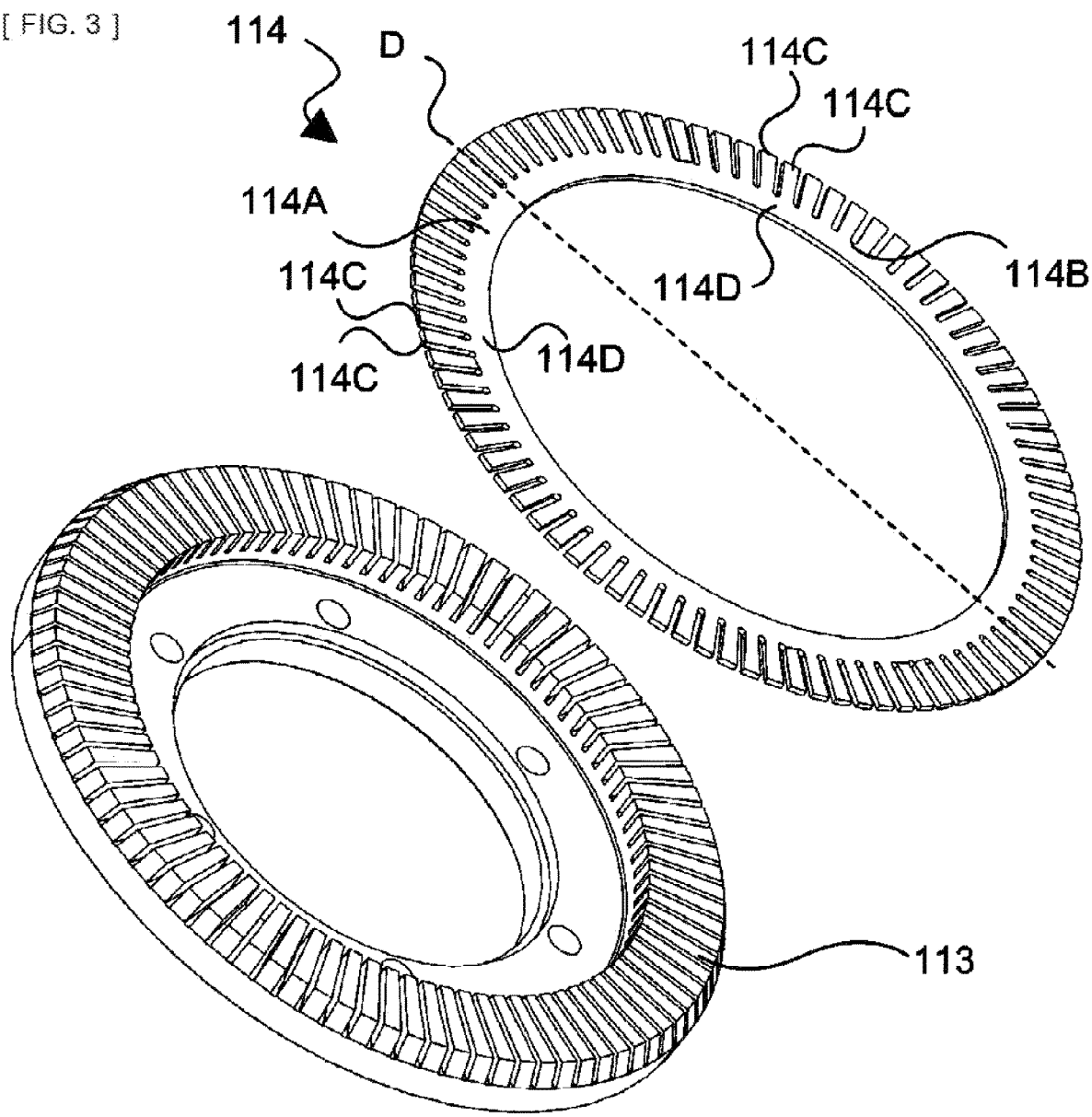
[FIG. 3]

[ FIG. 4 ]
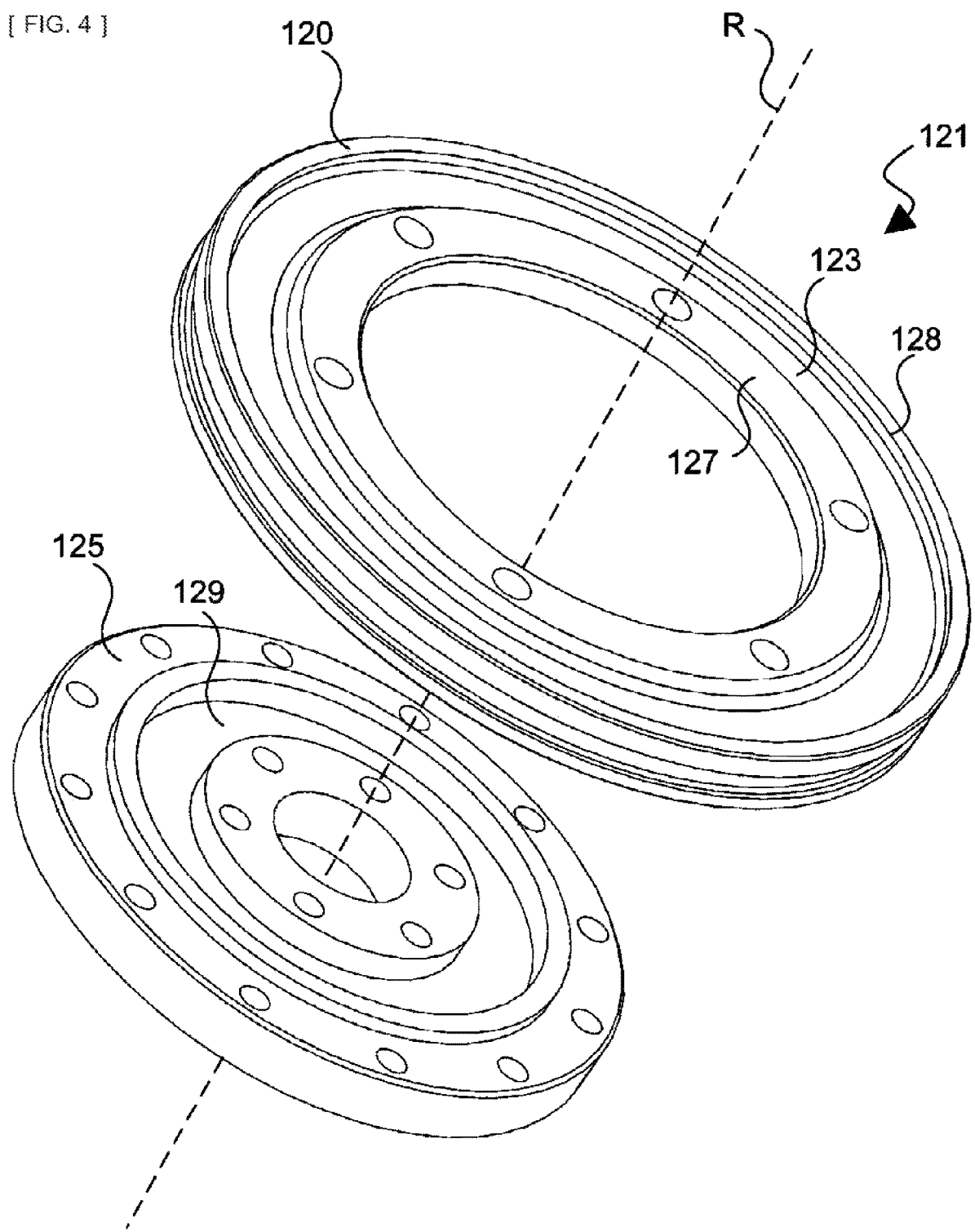

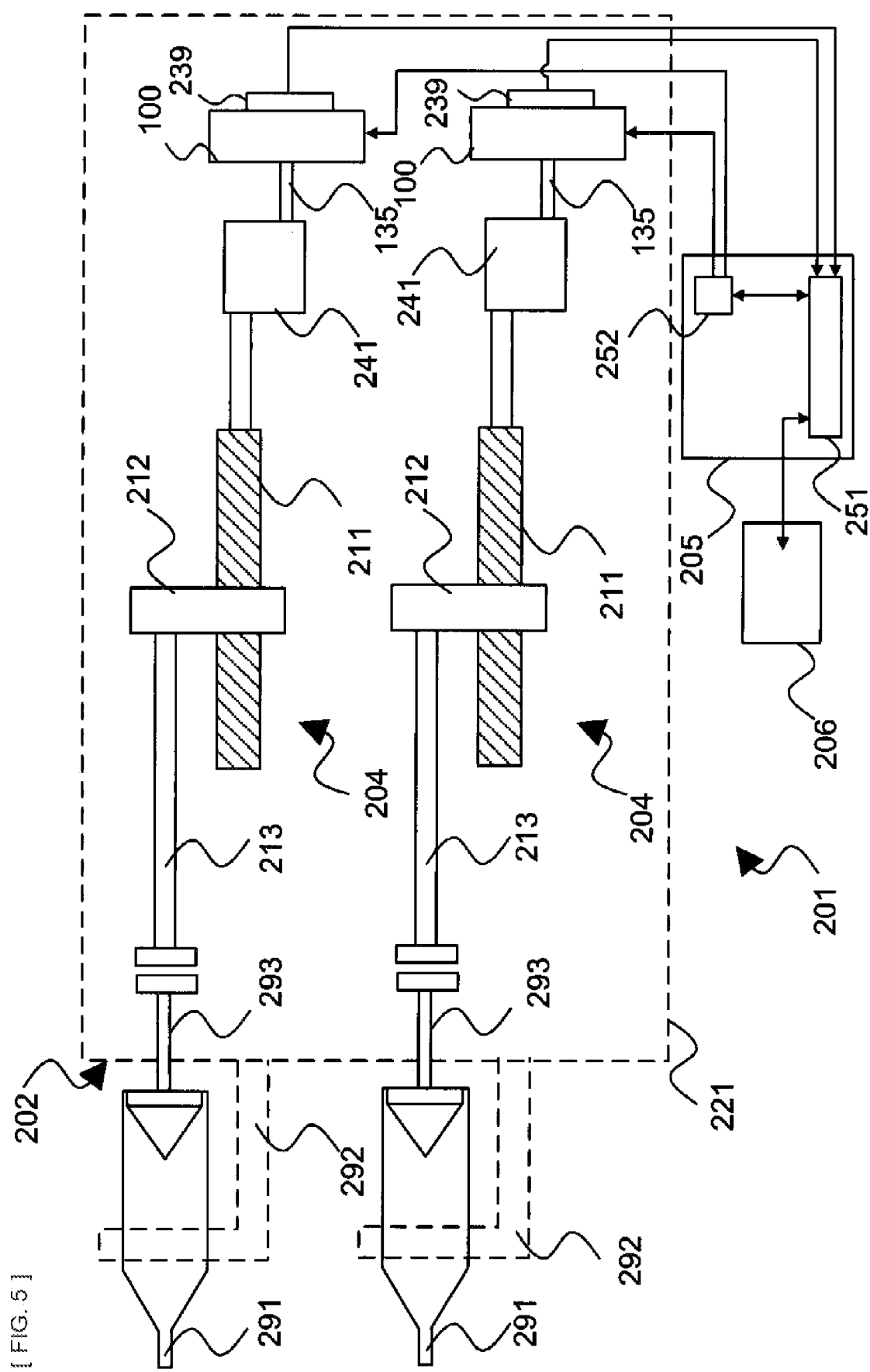
[FIG. 5]

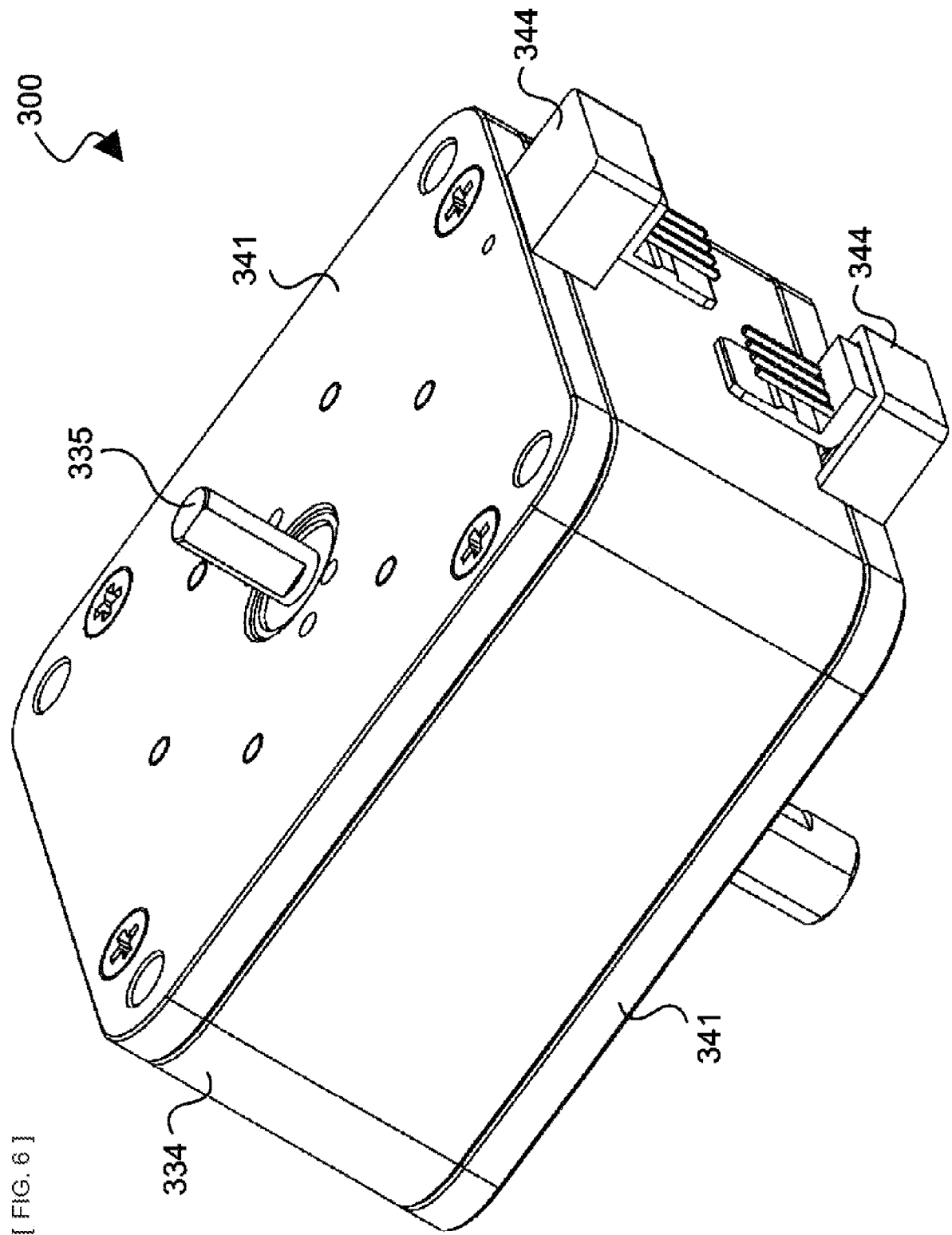
[ FIG. 6 ]

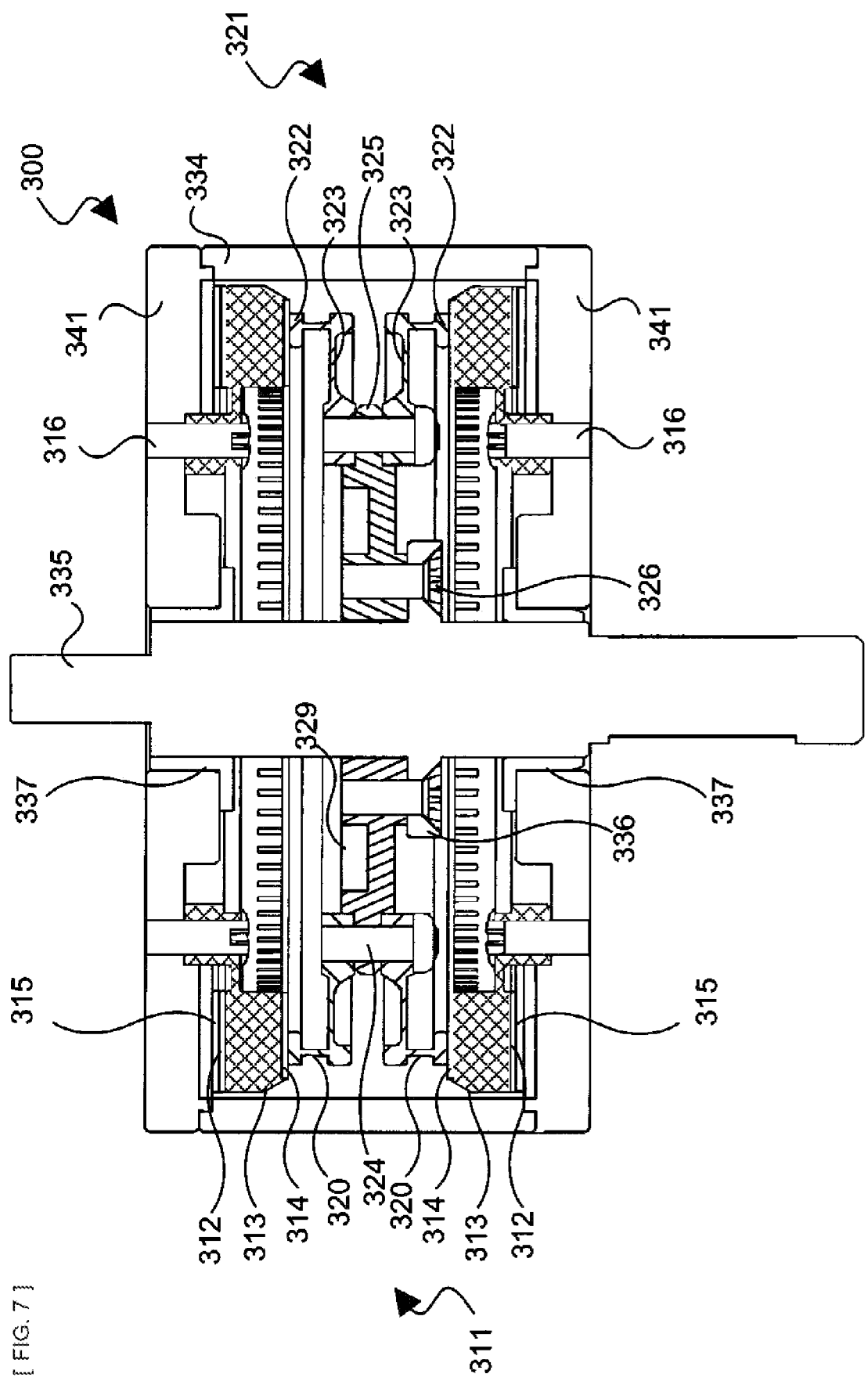

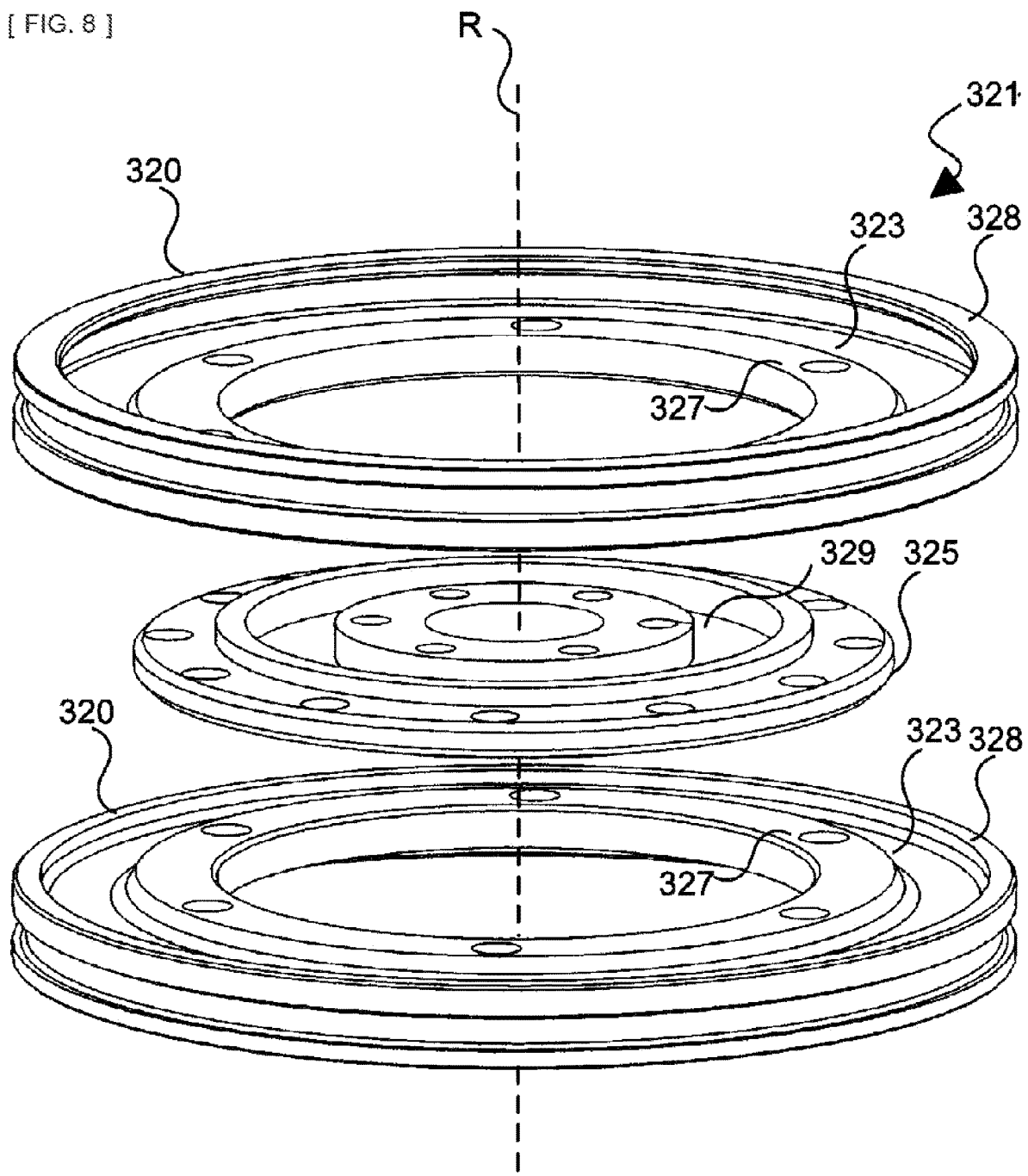
[FIG. 8]

PIEZOELECTRIC MOTOR AND INJECTION DEVICE

CROSS-REFERENCE TO RELATED PATENT APPLICATIONS

This application is a U.S. National Phase application under 35 U.S.C. § 371 of International Patent Application No. PCT/JP2019/030568 filed on Aug. 2, 2018 and claims the benefit of priority to Japanese Patent Applications No. 2018-151666, filed Aug. 10, 2018, all of which are incorporated herein by reference in their entireties. The International Application was published in Japanese on Feb. 13, 2020 as International Publication No. WO/2020/031910 under PCT Article 21(2).

FIELD OF THE INVENTION

The present invention relates to a piezoelectric motor and an injection device equipped with the piezoelectric motor.

BACKGROUND OF THE INVENTION

JP 2013-005712A discloses a piezoelectric motor (e.g., an ultrasonic motor) that utilizes a piezoelectric element to generate a driving force. The piezoelectric motor includes a stator fixed to a base, and a rotor fixed to a flange of a shaft. The stator has a piezoelectric element, an elastic body and a sliding member, which are arranged in this order. The rotor has a disc spring portion, and a basic body portion in contact with a sliding body of the stator. The disc spring portion serves as a spring to bias the rotor against the stator and extends from the basic body portion to the center of the rotor.

CITATION LIST

Patent Literature

Patent Literature 1: JP 2013-005712A

When a high frequency voltage is applied to the piezoelectric element of the stator, flexural vibrations occur in the elastic body due to expansion and contraction of the piezoelectric element such that traveling waves are generated in the circumferential direction. Since the rotor is in contact with the elastic body through the sliding member, the rotor rotates in a direction opposite to the traveling waves when the traveling waves are generated. Upon the rotation of the rotor, the shaft rotates in the same direction as the rotor.

Technical Problem

The basic body portion of the rotor moves in one direction due to the deflection of the elastic body, and then moves in the opposite direction due to the biasing force of the disc spring portion. Therefore, vibrations caused by the reciprocating motion of the basic body portion may occur in the disc spring portion which is integrally formed with the basic body portion. If the vibrations of the disc spring portion continue, it becomes a cause for abnormal noises. Furthermore, the life of the piezoelectric motor is shortened because the disc spring portion may be damaged by vibrations.

SUMMARY OF THE INVENTION

Solution to Problem

To solve the above-described problems, as an example of the present invention, a piezoelectric motor comprising: a stator having an elastic body, and a piezoelectric element and a sliding member adhesively attached to the elastic body; a rotor having an annular member, which includes a disc spring portion and a basic body portion in contact with the sliding member, and a fixture portion to which the annular member is fixed; and a shaft that rotates with the rotor, wherein the disc spring portion of the annular member is fixed to the fixture portion which is fixed to the shaft.

As another example of the present invention, an injection device is an injection device for injecting a chemical liquid, comprising: the piezoelectric motor; a drive mechanism driven by the piezoelectric motor; and a control device controlling the piezoelectric motor.

Further features of the present invention will become apparent from the following description of embodiments illustrated exemplarily with reference to the accompanying drawings.

BRIEF DESCRIPTION OF THE DRAWINGS

FIG. 1 is a schematic perspective view of a piezoelectric motor according to a first embodiment of the present invention.

FIG. 2 is a schematic cross-sectional view of the piezoelectric motor.

FIG. 3 is a schematic perspective view of a sliding member.

FIG. 4 is a schematic perspective view of a rotor of the piezoelectric motor.

FIG. 5 is a schematic block diagram of an injection device.

FIG. 6 is a schematic perspective view of a piezoelectric motor according to a second embodiment of the present invention.

FIG. 7 is a schematic cross-sectional view of a piezoelectric motor.

FIG. 8 is a schematic perspective view of a rotor of the piezoelectric motor.

DETAILED DESCRIPTION OF THE INVENTION

Hereinafter, exemplary embodiments for carrying out the present invention will be described in detail with reference to drawings. It should be noted, however, that dimensions, materials, shapes, and relative positions between components described in the following embodiments are arbitrary and can be changed depending on the configuration or various conditions of the device to which the present invention is applied. Also, unless otherwise mentioned, the scope of the present invention is not limited to the embodiments specifically described below.

First Embodiment

A piezoelectric motor 100 of the first embodiment will be described with reference to FIG. 1 to FIG. 4. FIG. 1 is a perspective view of a piezoelectric motor 100 of the first embodiment and shows the appearance as viewed from a case 134. FIG. 2 is a schematic cross-sectional view along the longitudinal direction of a shaft 135 and shows a cross-section through a rotation axis of the shaft 135. FIG. 3 is a schematic perspective view of a sliding member 114. FIG. 4 is a schematic perspective view of a rotor 121 of the piezoelectric motor 100.

As shown in FIG. 1, the piezoelectric motor 100 includes a base 141 and the case 134 which is screwed to the base 141. Further, the piezoelectric motor 100 includes the shaft 135 which penetrates the base 141 and the case 134 and protrudes from the base 141 and the case 134. Further, a connector 144 for connecting to the outside is attached to a side face of the substantially plate-shaped base 141 via a terminal support plate.

As shown in FIG. 2, the piezoelectric motor 100 has a configuration substantially rotation-symmetrical about the rotation axis of the shaft 135. The piezoelectric motor 100 includes a stator 111 fixed to the base 141, and the rotor 121 that faces the stator 111. The stator 111 and the rotor 121 are received in a substantially cylindrical space in the case 134. The stator 111 includes an elastic body 113, and a piezoelectric element 112 adhesively attached to the elastic body 113, and the sliding member 114 adhesively attached to the elastic body 113. The rotor 121 includes an annular member 120, and the annular member 120 has a basic body portion 122 in contact with the sliding member 114, and a disc spring portion 123 which is integrally formed with the basic body portion 122. The shaft 135 extends through the stator 111, which has a substantially ring shape, and the rotor 121, which also has a substantially ring shape. The stator 111 and the rotor 121 are coaxial with the rotation axis of the shaft 135.

Further, the piezoelectric motor 100 includes a flexible substrate 115 which is electrically connected to the piezoelectric element 112. The flexible substrate 115 is electrically connected to the connector 144. A high-frequency voltage is applied to the piezoelectric element 112 from an external power source via the connector 144 and the flexible substrate 115. When the high-frequency voltage is applied, flexural vibrations occur in the elastic body 113 due to the expansion and contraction of the piezoelectric element 112, and traveling waves are generated in the circumferential direction. At each apex of the traveling wave, the rotor 121 is in contact with the elastic body 113 via the sliding member 114. Each apex is elliptically moving, and the locus of the elliptical motion is in the direction opposite to the traveling direction of the traveling wave. Therefore, the rotor 121 rotates in the direction opposite to the traveling wave.

The piezoelectric element 112 such as a piezo element, the elastic body 113 to which the piezoelectric element 112 is adhesively attached, and the sliding member 114 adhesively attached to the elastic body 113 are arranged in this order from the base 141 toward the rotor 121. The sliding member 114 may be configured such that the sliding member can suppress the deformation even when the basic body portion 122 is strongly pressed to the sliding member. As an example, the sliding member 114 can be formed of a crosslinked fluororesin containing reinforcing fibers. PTFE, PFA or FEP can be used as the fluororesin, and two or more kinds of fluororesins can be used. The reinforcing fiber is, for example, carbon fiber, glass fiber, metal fiber, silicon carbide fiber, silicon nitride fiber, aramid fiber, alumina fiber, polyamide fiber, polyethylene fiber, polyester fiber, ceramic fiber, PTFE fiber or boron fiber. By using the crosslinked fluororesin containing the reinforcing fibers, the reinforcing fibers suppress the deformation of the sliding member 114 when the basic body portion 122 of the rotor 121 is pressed against the sliding member 114. Thus, it is possible to increase the pressing force when the rotor 121 is pressed against the stator 111 (frictional force between the rotor and the stator), and increase the torque of the piezoelectric motor 100.

Further, the sliding member 114 may be formed from a cross-linked fluororesin (including the crosslinked fluororesin containing the reinforcing fibers) whose specific wear amount is $1 \times 10^{-6}$ mm$^3$/N·M or less when measured by a sliding wear test in accordance with the JISK7218A method (ring-to-disk). More desirably, the sliding member 114 may be formed from a crosslinked fluororesin whose specific wear amount is less than $1 \times 10^{-7}$ mm$^3$/N·M. The test conditions are as follows: the mating material was ADC12 whose arithmetic mean roughness (Ra) was 0.2 μm, the velocity was 128 m/min, time was 50 hours, and the load was 0.4 MPa. As a comparative example, the specific wear amount of a non-crosslinked PTFE was measured under the same conditions, and the measured specific wear was $1 \times 10^{-3}$ mm$^3$/N·M. By using the cross-linked fluororesin, it is possible to improve the wear resistance and extend the life of the sliding member 114. Consequently, it is possible to extend the life of the piezoelectric motor 100. The elastic body 113 includes a plurality of comb teeth. Between each two adjacent comb teeth, formed is a rectangular groove extending radially toward the outer periphery of the elastic body 113 from the center of the elastic body 113. As an example, the elastic body 113 can be formed of a metal such as iron, steel, duralumin, copper alloy and titanium alloy.

As shown in FIG. 3, the sliding member 114 includes a first sliding portion 114A having a substantially semicircular outer shape and a second sliding portion 114B having also a substantially semicircular outer shape. Each of the first sliding portion 114A and the second sliding portion 114B includes a plurality of sliding pieces 114C facing each other across respective slits, and a bridge 114D for connecting the sliding pieces 114C. The first sliding portion 114A and the second sliding portion 114B are divided by a dividing line D indicated by the broken line in FIG. 3. Alternatively, the sliding member 114 having a substantially circular outer shape may be formed without dividing, and the sliding member 114 may be configured to have the sliding pieces 114C and the bridge 114D. Alternatively, the sliding member 114 may be divided into three or more portions such that a plurality of sliding portions, each having a substantially arcuate outer shape, are formed.

The sliding pieces 114C are connected to each other by the bridge 114D, which is an inner edge of the sliding member 114. By aligning the position of the bridge 114D of the first sliding portion 114A with the position of the bridge 114D of the second sliding portion 114B, the two bridges 114D are arranged in a substantially ring-shape. As shown in FIG. 2, the bridges 114D are set at the positions not in contact with the basic body portion 122. Therefore, even if the slits are not formed in the bridges 114D, it is possible to reduce the effect on the elliptical motion of the sliding member 114. Alternatively, the bridges 114D may be formed on the outer edge of the sliding member 114. Also, the bridges 114D may be formed on both the outer edge and the inner edge of the sliding member 114. In this configuration, slits, each having a substantially rectangular outer shape, are formed in the sliding member 114.

As an example, the adhesive attachment of the sliding member 114 can be done as follows. Firstly, a sheet-like base material of the sliding member 114 is prepared. Next, a plurality of portions serving as the first sliding portion 114A and the second sliding portion 114B are cut out from the base material such that each of the cut portions has a substantially semicircular outer shape. Then, the first sliding portion 114A and the second sliding portion 114B are aligned such that the sliding pieces 114C are respectively positioned on the comb teeth of the elastic body 113, and the sliding member 114 is attached to the elastic body 113 with an adhesive. At this time, since the sliding pieces 114C are connected by the bridge 114D, the workability of the attachment with the adhesive is improved.

Thereafter, the piezoelectric element 112 is attached to the elastic body 113 with an adhesive, and the flexible substrate 115 is attached to the piezoelectric element 112 with an adhesive. Then, the elastic body 113 is screwed to the base 141. Alternatively, after adhesively attaching the piezoelectric element 112 to the elastic body 113, the sliding member 114 may be adhesively attached. Here, the slit is formed in the sliding member 114 before attaching with the adhesive. Therefore, it is possible to suppress a possibility that the surface of the sliding member 114 is distorted upon forming the slit, after attaching with the adhesive, around the portion in contact with the basic body portion 122. It should be noted that a press working may be carried out after adhesive attachment of the sliding member 114 such that the bridge 114D is divided at a position corresponding to the groove between the comb teeth of the elastic member 113. In this configuration, since there is no need to form a slit in the portion in contact with the basic body portion 122, the surface of the sliding member 114 is prevented from being distorted in the portion in contact with the basic body portion 122.

Referring back to FIG. 2, the shaft 135 rotates with the rotation of the rotor 121 in the same direction as the rotor 121. The base 141 has a hole formed therein, through which the shaft 135 penetrates. A bushing 137 is received in this hole by press-fitting. Alternatively, a bearing may be used in place of the bushing 137. Further, a hole through which the shaft 135 penetrates is also formed in the case 134, and a bearing 138 is mounted at a position corresponding to the hole. The shaft 135 extends through the bushing 137 and the bearing 138, respectively.

The stator 111 is fixed to the base 141 by a plurality of stator screws 116. Specifically, the edge of the elastic body 113 on the shaft 135 side has screw holes (not shown). Further, the base 141 has screw holes corresponding to the screw holes of the elastic body 113. As the stator screws 116 are screwed into both of the screw holes of the elastic body and the screw holes of the base, the stator 111 is fixed to the base 141.

The rotor 121 has a stabilizer 125 which is fixed to the shaft 135 as an example of a fixture portion to which the disc spring portion 123 of the annular member 120 is fixed. As shown in FIG. 4, a bore is formed in the center of the annular member 120, and the annular member 120 and the stabilizer 125 are separate from each other. The rotor 121 is fixed to a flange 136 of the shaft 135 through a plurality of first rotor screws 124, the stabilizer 125, and a plurality of second rotor screws 126. An inner edge 127 located on the shaft 135 side of the disc spring portion 123 of the annular member 120 has the screw holes. An outer edge of the stabilizer 125 has the screw holes corresponding to the screw holes of the annular member. As the first rotor screws 124 (FIG. 2) are screwed into both of the screw holes of the annular member and the screw holes of the stabilizer, the disc spring portion 123 is fixed to the stabilizer 125.

The disc spring portion 123 serves as a spring to bias the rotor 121 to the stator 111. Thus, the basic body portion 122 is pressed against the sliding member 114 of the stator 111. That is, as the disc spring portion 123 biases the basic body portion 122 to the stator 111, the rotor 121 is brought into close contact with the sliding member 114. Because the disc spring portion 123 functions as a spring, it is possible to reduce the size of the piezoelectric motor 100.

Further, as shown in FIG. 2, the disc spring portion 123 is provided between the basic body portion 122 and the stabilizer 125 in the radial direction of the piezoelectric motor 100. In other words, the stabilizer 125 is secured to the shaft 135 at a position closer to the shaft 135 than the disc spring portion 123. Specifically, the inner edge of the stabilizer 125 and the flange 136 of the shaft 135 are formed with the corresponding screw holes, respectively. As the second rotor screws 126 are screwed into both of the screw holes of the stabilizer and the screw holes of the flange, the stabilizer 125 is fixed to the flange 136.

The stabilizer 125 is formed thicker than a curved thin portion of the disc spring portion 123. That is, in the direction of the rotation axis of the shaft 135, the stabilizer 125 is thicker than the thin portion of the disc spring portion 123. The stabilizer 125 is configured such that the vibrations of the disc spring portion 123 propagate to the stabilizer. Thus, it is possible to suppress the vibrations of the disc spring portion 123 and reduce the abnormal noise. As a result of suppressing the vibrations, it is possible to extend the life of the piezoelectric motor 100. Incidentally, since the stabilizer 125 is thick, it is unlikely that the stabilizer will be damaged even if the vibrations propagate from the disc spring portion 123. The stabilizer 125 may be formed to be larger in mass than the annular member 120. Incidentally, the stabilizer 125 may be subjected to an alumite process or an annealing treatment.

In addition, the stabilizer 125 can shorten the distance from the inner edge 127 of the disc spring portion 123 to the outer edge 128 of the disc spring portion 123. In other words, the length of the disc spring portion 123 in the radial direction of the rotor 121 can be shorter than the conventional arrangement. Thus, the thin portion which is easily damaged can be shortened and therefore it is possible to reduce the possibility that the disc spring portion 123 is damaged. As a result, the life of the piezoelectric motor 100 can be extended. Further, no breakage would occur even if the rotor 121 is pressed against the stator 111 with a stronger force, and therefore it is possible to increase the torque of the piezoelectric motor 100. Furthermore, since the thin portion requiring high-precision processing can be shortened, it is also possible to reduce the manufacturing cost of the disc spring portion 123. In addition, it is possible to suppress the deformation of the disc spring portion 123 to a small amount and increase the torque of the piezoelectric motor 100. Further, as a result of a fact that the mass of the annular member 120 located outside the stabilizer 125 becomes small, it is possible to reduce the moment of inertia of the rotor 121. Therefore, it is possible to improve the responsiveness of the piezoelectric motor 100.

The disc spring portion 123 is screwed to the stabilizer 125 by the first rotor screws 124. The stabilizer 125 is screwed to the flange 136 of the shaft 135 by the second rotor screws 126. Screwing allows the disc spring portion 123 to be rigidly secured to the stabilizer 125 and also allows the stabilizer 125 to be rigidly secured to the shaft 135.

The screwing direction of each of the second rotor screws 126 in FIG. 2 is the opposite direction to the screwing direction of each of the first rotor screws 124. That is, each of the first rotor screws 124 is screwed toward the base 141 from the case 134 side. In contrast, each of the second rotor screws 126 is screwed toward the case 134 from the base 141 side. As an example, firstly, the rotor 121 is attached to the stabilizer 125 by the first rotor screws 124 screwed in one direction. Then, the stabilizer 125 is attached to the shaft 135 by the second rotor screws 126, which are screwed in the opposite direction.

It should be noted, however, that the screwing direction when fixing the stabilizer 125 to the shaft 135 may be the same direction as the screwing direction when fixing the disc spring portion 123 to the stabilizer 125. That is, the screw holes may be formed in the stabilizer 125 and the flange 136 such that the second rotor screws 126 can be screwed from the case 134 side toward the base 141. By screwing the second rotor screws 126 and the first rotor screws 124 in the same direction, the tightening direction by both screws coincide with each other. Therefore, the rotor 121 can be more firmly fixed to the shaft 135.

The stabilizer 125 may be made of metal. By way of example, the stabilizer 125 may be formed of a 5000 series aluminum alloy (e.g., A5052). Thus, when attaching the case 134 to the base 141, it is possible to suppress the deformation of the stabilizer 125 to a small amount. Therefore, it is possible to increase the pressing force when the rotor 121 is pressed against the stator 111 (frictional force between the rotor and the stator) and enhance the torque of the piezoelectric motor 100. Furthermore, it is also possible to suppress variations in the pressing force between the rotor and the stator. That is, when attaching the case 134, the stabilizer 125 is pressed against the base 141 (stator 111) side. Thus, although the rotor 121 is pressed against the stator 111, it is possible to suppress the variations in the pressing force due to a large deformation of the stabilizer 125. Incidentally, the annular member 120 can be formed of, for example, a 7000 series aluminum alloy (e.g., A7075).

Further, the stabilizer 125 may be configured to have a lower rigidity than the annular member 120 (such that the longitudinal elastic modulus is lowered). Thus, the stabilizer 125 absorbs the vibrations such that the vibrations of the disc spring portion 123 can be further suppressed by the stabilizer. To this end, the stabilizer 125 has an annular groove 129 about the rotation axis R of the shaft 135 shown by the dotted line in FIG. 4. The annular groove 129 has a generally U-shaped cross-section, and the bottom of the annular groove 129 is thinner than other portions of the stabilizer 125. The annular groove 129 decreases the rigidity of the stabilizer 125. As a result, it is possible to further suppress the vibrations of the disc spring portion 123. Because the stabilizer 125 is configured in this manner with low rigidity, the stabilizer 125 slightly deforms when the rotor 121 is pressed against the stator 111. As a result, it is possible to evenly distribute the force pressing the rotor 121 to the stator 111. Incidentally, the stabilizer 125 may be configured to have the same rigidity as the annular member 120 or a higher rigidity than the annular member 120. It should be noted, however, that if the stabilizer is configured to have low rigidity, it is possible to further suppress the vibrations of the disc spring portion 123. Incidentally, although the single annular groove 129 is formed in FIG. 4, two or more annular grooves 129 may be formed.

The width of the substantially ring-shaped stabilizer 125 in the radial direction is set longer than the width of the substantially ring-shaped disc spring portion 123 in the radial direction. Thus, the mass of the stabilizer 125 can be greater than a corresponding portion of the disc spring portion 123 over the entire circumference of the disc spring portion 123. Therefore, the rigidity of the stabilizer 125 can be lower than the disc spring portion 123 over the entire circumference of the disc spring portion 123. It should be noted, however, that as a modification, the shape of the stabilizer 125 is not limited to the ring shape, i.e., the stabilizer may have other shapes such as a polygon.

Incidentally, a spacer may be disposed between the bearing 138 and the stabilizer 125. With this configuration, when attaching the case 134 to the base 141, it is possible to adjust the pressing force when the rotor 121 is pressed against the stator 111. A spring, e.g., a disc spring, may be disposed between the bearing 138 and the stabilizer 125 in place of or in addition to the spacer. This configuration increases the pressing force when the rotor 121 is pressed against the stator 111, and it is possible to enhance the torque of the piezoelectric motor 100. Specifically, if a disc spring which is convex toward the stabilizer 125 is disposed, the rotor 121 can be pressed against the stator 111.

According to the piezoelectric motor 100 according to the first embodiment, the provision of the stabilizer 125 can suppress the vibrations of the disc spring portion 123 which is integrally formed with the basic body portion 122. Therefore, it is possible to reduce the abnormal noise, suppress the damage to the disc spring portion 123 and extend the life of the piezoelectric motor 100.

Injection Device

Next, an injection device 201 will be described with reference to FIG. 5, which is a block diagram. Since the configuration of the piezoelectric motor 100 has been described above, the description thereof will be omitted.

As shown in FIG. 5, the injection device 201 for injecting a chemical liquid includes the piezoelectric motors 100, drive mechanisms 204 driven by the piezoelectric motors 100, respectively, and a control device 205 for controlling the piezoelectric motors 100. Each of the drive mechanisms 204 is driven so as to feed the chemical liquid when the piezoelectric motor 100 rotates in a forward direction. The drive mechanisms 204 and the piezoelectric motors 100 are housed in a frame 221 of an injection head 202 of the injection device 201. If the location of each syringe holder 292 is referred to as a front side, each piezoelectric motor 100 is disposed on the rear side in the frame 221.

The frame 221 has the two syringe holders 292 to hold the two cylinders 291. The injection device 201 has a console 206 on which an injection state of the chemical liquid or the like is displayed. The console 206 is connected to the control device 205 via an optical cable and the control device 205 is connected to the injection head 202. The control device 205 and console 206 are also connected to an external power source inside an examination room or outside the examination room, and the control device 205 also serves as a power supply.

The control device 205 includes a CPU 251 for controlling the piezoelectric motor 100, and a drive circuit 252 for applying a high-frequency voltage to the piezoelectric motor 100. The CPU 251 is electrically connected to the drive circuit 252 to transmit a drive signal to the piezoelectric motor 100. Further, the drive circuit 252 is electrically connected to the piezoelectric motor 100. An encoder 239 is connected to the piezoelectric motor 100, and transmits information such as the presence or absence of the rotation and the rotational speed of the piezoelectric motor 100 to the control device 205.

Each of the drive mechanisms 204 includes a transmission mechanism 241, a ball screw shaft 211, a ball screw nut 212, and an actuator 213. The drive mechanism 204 is disposed between the syringe holder 292 and the piezoelectric motor 100. The transmission mechanism 241 is connected to the shaft 135 of the piezoelectric motor 100, the ball screw shaft 211 is connected to the transmission mechanism 241. The ball screw nut 212 is attached to the ball screw shaft 211 and the actuator 213 is connected to the ball screw nut 212.

Each of the transmission mechanisms 241 includes a pinion gear connected to the shaft 135, and a screw gear connected to the ball screw shaft 211 (not shown). The transmission mechanism 241 transmits the rotation of the piezoelectric motor 100 to the ball screw shaft 211. Therefore, the rotation of the shaft 135 of the piezoelectric motor 100 is transmitted to the ball screw shaft 211 via the pinion gear and the screw gear.

The ball screw shaft 211 rotates in accordance with the rotation transmitted from the shaft 135. The ball screw nut 212 slides in the forward direction (toward the front) or the backward direction (toward the rear) as the ball screw shaft 211 rotates. As a result, when the ball screw nut 212 slides, the actuator 213 moves forward or backward. That is, the actuator 213 moves forward when the shaft 135 rotates in the forward direction whereas the actuator 213 moves backward when the shaft 135 rotates in the reverse direction.

A piston 293 which is slidable in the cylinder 291 is provided for each cylinder 291 mounted on the syringe holder 292. The cylinder 291 is mounted such that a rod of the piston 293 abuts against the front end of the actuator 213. Thus, when the ball screw nut 212 slides in the forward direction while the cylinder 291 is mounted, the actuator 213 will push the piston 293 in the forward direction. When the piston 293 moves forward, the chemical liquid in the cylinder 291 is pushed out, and is injected into the patient's body through a catheter or the like connected to the front end of the cylinder 291. When the ball screw nut 212 slides in the backward direction, the actuator 213 will pull the piston 293 in the backward direction.

When injecting the chemical liquid, a user mounts the two cylinders 291 filled with the chemical liquid on the syringe holders 292 and turns on the power of the injection device 201. Thereafter, when the user presses the injection button, the control device 205 sends a forward rotation signal as a drive signal to the piezoelectric motor 100. The piezoelectric motor 100 is driven in response to the forward rotation signal, and the shaft 135 rotates in the forward direction. When the shaft 135 rotates in the forward direction, the chemical liquid is injected and the encoder 239 detects the rotation and sends a pulse signal to the control device 205.

When the injection is finished and the cylinder 291 is removed, the control device 205 sends a reverse rotation signal as a drive signal to the piezoelectric motor 100 to cause the piston 293 to move backward. The piezoelectric motor 100 is driven in response to the reverse rotation signal, and the shaft 135 rotates in the reverse direction. Incidentally, the drive signal transmitted to the piezoelectric motor 100 is an AC signal. Thus, if a drive signal is referred to as the forward rotation signal when one of the two signals having different phases is delayed with respect to the other, the drive signal is referred to as the reverse rotation signal when the other is delayed with respect to one of the two signals.

The control device 205 stores the injection protocol in advance, and the injection of the chemical liquid is carried out automatically in accordance with the injection protocol. The injection protocol includes, for example, injection time, injection speed, injection volume and injection pressure limit values. The control device 205 monitors the injection status, and automatically stops the injection of the chemical liquid when the control device detects an abnormality such as a decrease in the injection pressure. Incidentally, the injection pressure can be detected by a load cell attached to the front end of the actuator 213.

The piezoelectric motor 100 can be configured using a non-magnetic material. As examples of the non-magnetic material, the material of the elastic body 113 is phosphor bronze, and the material of the shaft 135, the second rotor screw 126, the first rotor screw 124, and the stator screw 116 is brass. The material of the case 134, the base 141, the disc spring portion 123, and the stabilizer 125 is aluminum, and the material of the bushing 137 is a fluororesin.

If the piezoelectric motor 100 is configured using the non-magnetic material, the injection device 201 can be used in the vicinity of a machine or equipment that utilizes magnetism such as an MRI (Magnetic Resonance Imaging) device. The injection device 201 may be used with, for example, a CT (Computed Tomography) device, an angio imaging device, a PET (Positron Emission Tomography) device, a SPECT (Single Photon Emission Computed Tomography) device, a CT angio device, an MR angio device, an ultrasonic diagnostic device or a blood vessel imaging device. In this case, the piezoelectric motor 100 can be configured using a magnetic material.

In the injection device 201, because the piezoelectric motor 100 is provided with the stabilizer 125, it is possible to suppress the vibrations of the disc spring portion 123. Therefore, it is possible to reduce the abnormal noise, suppress the damage to the disc spring portion 123, and extend the life of the piezoelectric motor 100. Thus, it is possible to extend the life of the injection device 201.

Second Embodiment

A piezoelectric motor 300 of the second embodiment will be described with reference to FIG. 6 to FIG. 8. FIG. 6 is a perspective view of the piezoelectric motor 300 of the second embodiment. FIG. 7 is a schematic cross-sectional view along a longitudinal direction of a shaft 335 and shows a cross-section through the rotation axis of the shaft 335. FIG. 8 is a schematic perspective view of a rotor 321 of the piezoelectric motor 300. In the second embodiment, a stator further includes another elastic body, another piezoelectric element, and another sliding member. Also, the rotor further includes another basic body portion and another disc spring portion.

As shown in FIG. 6, the piezoelectric motor 300 has a case 334 which is fixed to a pair of bases 341. Each of the two bases 341 has a substantially plate-like shape, and screwed to the case 334. Further, the piezoelectric motor 300 includes the shaft 335 which penetrates the base 341 and the case 334 such that the shaft protrudes from the base 341 and the case 334. The shaft 335 penetrates the stator 311, which has a substantially ring shape, and the rotor 321, which also has substantially ring shape, and rotates with the rotor 321. On a side surface of each of the bases 341, a connector 344 for connecting to the outside is attached via a terminal support plate.

As shown in FIG. 7, the piezoelectric motor 300 has a configuration substantially rotation-symmetrical about the rotation axis of the shaft 335. The piezoelectric motor 300 includes the stator 311 fixed to the bases 341, and the rotor 321 that faces the stator 311. The stator 311 and the rotor 321 are received in a substantially cylindrical space in the case 334. The shaft 335 extends through the stator 311 and the rotor 321 each having a substantially ring shape. The stator 311 and the rotor 321 are coaxial with the rotation axis of the shaft 335.

The stator 311 of the second embodiment has two elastic bodies 313, two piezoelectric elements 312, and two sliding members 314. Each piezoelectric element 312 and each sliding member 314 are adhesively attached to the associated elastic body 313. The rotor 321 includes two annular members 320 each having a basic body portion 322 and a disc spring portion 323. Each basic body portion 322 abuts the associated sliding member 314, and each dish spring portion 323 is integrally formed with the associated basic body portion 322. Further, the rotor 321 has a stabilizer 325 as an example of a fixture portion to which the disc spring portions 323 of the two annular members 320 are fixed and which is fixed to the shaft 335.

On both sides of the piezoelectric motor 300, the piezoelectric elements 312, the elastic bodies 313 and the sliding members 314 are arranged in this order from the bases 341 toward the rotor 321, respectively. Further, the piezoelectric motor 300 includes flexible substrates 315 which are electrically connected to the piezoelectric elements 312, respectively. The two flexible substrates 315 are electrically connected to the connectors 344. A high-frequency voltage is applied to each piezoelectric element 312 from an external power source via the associated connector 344 and the associated flexible substrate 315.

A hole through which the shaft 335 extends is formed in each of the two bases 341, and a bushing 337 is mounted in each hole by press-fitting. The shaft 335 extends through the two bushings 337, respectively. Alternatively, bearings may be used in place of the bushings 337. Further, each part in the stator 311 is fixed to the associated base 341 by a plurality of stator screws 316. Specifically, the edge of the elastic body 313 on the shaft 335 side has screw holes. Further, each of the bases 341 has screw holes corresponding to the screw holes of the associated elastic body 313. As the stator screws 316 are screwed into both of the screw holes of the elastic body and the base, the stator 311 is fixed to the base 341.

The rotor 321 is fixed to a flange 336 of the shaft 335 through a plurality of first rotor screws 324, the stabilizer 325, and a plurality of second rotor screws 326. The rotor 321 has the single stabilizer 325 to which the two disc spring portions 323 are secured. Specifically, an inner edge 327 (FIG. 8) of each disc spring portion 323 on the shaft 335 side has screw holes. An outer edge of the stabilizer 325 has screw holes corresponding to the screw holes of the disc spring portion. As the first rotor screws 324 are screwed into both of the screw holes of the stabilizer and the screw holes of each dish spring portion, each disc spring portion 323 is fixed to the stabilizer 325.

One of the disc spring portions 323 is fixed to one side of the stabilizer 325, and the other of the disc spring portions 323 is fixed to the other side of the stabilizer, which is opposite to the above-mentioned one side. The outer edge of the stabilizer 325 is sandwiched between the inner edges 327 of the two disc spring portions 323. Each of the disc spring portions 323 is provided between the associated base portion 322 and the stabilizer 325 in the radial direction of the piezoelectric motor 300. In other words, the stabilizer 325 is secured to the shaft 335 at a position closer to the shaft 335 than the disc spring portions 323. Specifically, the inner edge of the stabilizer 325 and the flange 336 of the shaft 335 are formed with corresponding screw holes, respectively. As the second rotor screws 326 are screwed into both of the screw holes of the stabilizer and the screw holes of the shaft flange, the stabilizer 325 is fixed to the flange 336.

Alternatively, the rotor 321 may further include another stabilizer 325. In this configuration, one of the disc spring portions 323 is secured to the above-mentioned "another stabilizer 325." That is, the two stabilizers 325 are disposed at positions facing the elastic bodies 313, respectively. Also, two flanges 336 are formed on the shaft 335 such that the two stabilizers 325 are screwed to the two flanges, respectively. When another stabilizer 325 is provided, the stabilizer 125 of the first embodiment can be used and therefore the number of parts can be reduced. On the other hand, when the rotor 321 includes only one stabilizer 325, the piezoelectric motor 300 can have a smaller size.

In the direction of the rotation axis of the shaft 335, the stabilizer 325 is thicker than a thin portion of the disc spring portion 323. The stabilizer 325 is configured such that the vibrations of each of the disc spring portions 323 propagate to the stabilizer. Thus, it is possible to suppress the vibrations of each of the disc spring portions 323 and reduce the abnormal noise. Further, as a result of suppressing the vibrations, it is possible to extend the life of the piezoelectric motor 300. In addition, the stabilizer 325 may be configured to be less rigid than the disc spring portions 323. Thus, the vibrations of the disc spring portions 323 can be further suppressed by the stabilizer 325.

Use of the stabilizer 325 can reduce the distance from the inner edge 327 of the disc spring portion 323 to the outer edge 328 of the disc spring portion 323 as compared to a conventional arrangement. Thus, the easily damaged thin portion can be shortened and therefore it is possible to reduce the possibility that the disc spring portion 323 is damaged. As a result, it is possible to further extend the life of the piezoelectric motor 300. Furthermore, since the thin portion requiring high-precision processing can be shortened, it is also possible to reduce the manufacturing cost of the disc spring portion 323. Further, it is possible to suppress the deformation of each disc spring portion 323 to a small amount and increase the torque of the piezoelectric motor 300.

The screwing direction of each of the second rotor screws 326 in FIG. 7 is the same direction as the screwing direction of each of the first rotor screws 324. That is, the screwing direction when fixing the stabilizer 325 to the shaft 335 is the same direction as the screwing direction when fixing each of the disc spring portions 323 to the stabilizer 325. Thus, the tightening direction of the first rotor screws matches the tightening direction of the second rotor screws. Therefore, the rotor 321 can be more firmly fixed to the shaft 335.

The stabilizer 325 may be made of metal. Thus, when attaching the case 334 to the bases 341, it is possible to suppress the deformation of the stabilizer 325 to a small mount. Therefore, it is possible to enhance the pressing force when the rotor 321 is pressed against the stator 311 (frictional force between the rotor and the stator) and increase the torque of the piezoelectric motor 300. It is also possible to suppress variations in the pressing force between the rotor and the stator.

The stabilizer 325 has an annular groove 329 about the rotation axis R of the shaft 335 indicated by a dotted line in FIG. 8. The annular groove 329 has a generally U-shaped cross-section, and the bottom of the annular groove 329 is thinner than other portions of the stabilizer 325. The rigidity of the stabilizer 325 is reduced by the annular groove 329. As a result, it is possible to further suppress the vibrations of the disc spring portions 323. Incidentally, although the sole annular groove 329 is formed in FIG. 8, two or more annular grooves 329 may be formed.

In the radial direction of the piezoelectric motor 300, the width of the stabilizer 325 is set longer than the width of each disc spring portion 323. Thus, the mass of the stabilizer 325 can be greater than a corresponding portion of the disc spring portion 323 over the entire circumference of the disc spring portion 323. Therefore, the rigidity of the stabilizer 325 is lower than the rigidity of the disc spring portion 323 over the entire circumference of the disc spring portion 323.

Incidentally, a spacer may be disposed between the flange 336 of the shaft 335 and the stabilizer 325. Thus, when attaching the case 334 to the bases 341, it is possible to adjust the pressing force for pressing the rotor 321 against the stator 311. A spring, e.g., a disc spring, may be disposed between the flange 336 and the stabilizer 325 in place of or in addition to the spacer. Thus, it is possible to increase the pressing force used to press the rotor 321 against the stator 311 and enhance the torque of the piezoelectric motor 300.

The piezoelectric motor 300 according to the second embodiment can suppress the vibrations of the disc spring portions 323 because it is equipped with the stabilizer 325. Therefore, it is possible to reduce the abnormal noise, suppress the damage to the disc spring portions 323 and extend the life of the piezoelectric motor 300. Furthermore, as compared to the first embodiment, it is possible to further increase the torque of the piezoelectric motor 300.

While the present invention has been described with reference to the respective embodiments, the present invention is not limited to the above-described embodiments. Inventions modified to the extent that they are not contrary to the present invention, and inventions equivalent to the present invention are also included in the present invention. In addition, each of the embodiments and each modification can be appropriately combined within a range not contrary to the present invention.

For example, a plurality of rotors 121 each having the stabilizer 125, the basic body portion 122 and the disc spring portion 123 may be provided. In this case, a plurality of stators 111 each having the piezoelectric element 112, the elastic body 113 and the sliding member 114 can be provided corresponding to the number of the rotors 121. Flanges 136 may also be formed on the shaft 135 such that the number of the flanges 136 corresponds to the number of the stabilizers 125. For example, when three rotors 121 are provided, three stators 111 are provided and three flanges 136 are formed on the shaft 135. Incidentally, four or more rotors 121 and stators 111 may be provided.

The fixing of the disc spring portions 123 and 323 and the fixing of the stabilizers 125 and 325 are not limited to screwing, and other fixing methods such as welding may be used, respectively. Further, in the above-described embodiments, the basic body portion(s) 122, 322 and the disc spring portion(s) 123, 323 are integrally formed. It should be noted, however, that after forming the basic body portion(s) 122, 322 and the disc spring portion(s) 123, 323, respectively, the basic body portion(s) and the disc spring portion(s) may be united by a method such as welding. Instead of the annular groove 129, 329, a plurality of holes or recesses may be formed such that the holes or recesses are arranged in a grid shape, a radially spreading shape, or a concentric shape. Furthermore, a number of holes or recesses may be formed at equal intervals, and a number of hollow or ring-shaped spaces may be formed in the stabilizers 125, 325. In this case, the stabilizer 125, 325 can be formed by three-dimensional shaping using a metallic material.

Part or all of the above-described embodiments may also be described as in the following appendices, but not limited thereto. Incidentally, when it is not necessary to suppress the vibrations (e.g., if the abnormal noise can be ignored), the rotor 121, 321 may not be provided with the stabilizer 125, 325. In this case, the disc spring portion(s) 123, 323 extends to the shaft 135, 335 and is fixed directly to the flange 136, 336.

Supplementary Note 1

A piezoelectric motor comprising:
a stator having an elastic body, and a piezoelectric element and a sliding member adhesively attached to the elastic body;
a rotor having an annular member, the annular member having a disc spring portion and a basic body portion in contact with the sliding member; and
a shaft that rotates with the rotor,
wherein the sliding member has a plurality of sliding pieces facing each other across a slit, and a bridge connecting the plurality of sliding pieces.

Supplementary Note 2

The piezoelectric motor according to Supplementary Note 1, wherein the plurality of sliding pieces are disposed at positions where they contact with the basic body portion, and
the bridge is disposed such that the bridge avoids a position in contact with the basic body portion.

Supplementary Note 3

The piezoelectric motor according to Supplementary Note 1 or 2, wherein the sliding member is made of a crosslinked fluororesin containing reinforcing fibers.

Supplementary Note 4

The piezoelectric motor according to any one of Supplementary Notes 1 to 3, wherein a specific wear amount of the sliding member is less than $1\times10^{-6}$ mm$^3$/N·M.

Supplementary Note 5

A piezoelectric motor comprising:
a stator having an elastic body, and a piezoelectric element and a sliding member adhesively attached to the elastic body;
a rotor having an annular member, the annular member having a disc spring portion and a basic body portion in contact with the sliding member; and
a shaft that rotates with the rotor,
wherein the sliding member is made of a crosslinked fluororesin containing reinforcing fibers.

Supplementary Note 6

The piezoelectric motor according to Supplementary Note 5, wherein a specific wear amount of the sliding member is less than $1\times10^{-6}$ mm$^3$/N·M.

This application claims a priority from Japanese Patent Application No. 2018-151666, filed Aug. 10, 2018, the entirety of which is incorporated herein by reference.

REFERENCE SINGS LIST

100: Piezoelectric motor, 111: Stator, 112: Piezoelectric element, 113: Elastic body, 114: Sliding member, 121: Rotor, 122: Basic body portion, 123: Disc spring portion, 125: Fixture portion, 129: Annular groove, 135: Shaft, 201: Injection device, 204: Drive mechanism, 205: Control device, 300: Piezoelectric motor, 311: Stator, 312: Piezoelectric element, 313: Elastic body, 314: Sliding member, 321: Rotor, 322: Basic body portion, 323: Disc spring portion, 325: Fixture portion, 329: Annular groove, 335: Shaft

What is claimed is:

1. A piezoelectric motor comprising:
a stator having an elastic body, and a piezoelectric element and a sliding member adhesively attached to the elastic body;
a rotor having an annular member, which includes a disc spring portion and a basic body portion in contact with the sliding member, and a fixture portion to which the annular member is fixed; and
a shaft that rotates with the rotor,
wherein the disc spring portion of the annular member is fixed to the fixture portion which is fixed to the shaft.

2. The piezoelectric motor according to claim 1, wherein the fixture portion is fixed to the shaft at a position closer to the shaft than the disc spring portion.

3. The piezoelectric motor according to claim 1, wherein rigidity of the fixture portion is lower than rigidity of the annular member.

4. The piezoelectric motor according to claim 1, wherein the fixture portion has an annular groove about a rotation axis of the shaft.

5. The piezoelectric motor according to claim 1, wherein the fixture portion is made of metal.

6. The piezoelectric motor according to claim 1, wherein a screwing direction when fixing the fixture portion to the shaft is the same direction as a screwing direction when fixing the disc spring portion to the fixture portion.

7. The piezoelectric motor according to claim 1, wherein the sliding member is made of a crosslinked fluororesin which contains reinforcing fibers, and
a specific wear amount of the sliding member is less than $1 \times 10^{-6}$ mm$^3$/N·M when measured by a sliding wear test.

8. The piezoelectric motor according to claim 1, wherein the stator further has another elastic body different from the elastic body, another piezoelectric element different from the piezoelectric element, and another sliding member different from the sliding member, and
the rotor further has another annular member which includes another basic body portion different from the basic body portion and another disc spring portion different from the disc spring portion.

9. The piezoelectric motor according to claim 8, wherein the disc spring portions is fixed to one side of the fixture portion, and
the other disc spring portions is fixed to another side of the fixture portion.

10. The piezoelectric motor according to claim 8, wherein the rotor further has another fixture portion different from the fixture portion, and
the other disc spring portions is fixed to the other fixture portion.

11. A piezoelectric motor comprising:
a stator having an elastic body, and a piezoelectric element and a sliding member adhesively attached to the elastic body;
a rotor having a disc spring portion, and a basic body portion in contact with the sliding member; and
a shaft that rotates with the rotor,
wherein an annular groove is formed between the disc spring portion and the shaft.

12. The piezoelectric motor according to claim 11, wherein a portion corresponding to a bottom of the annular groove is thicker than a thin portion of the disc spring portion.

13. An injection device for injecting a chemical liquid comprising:
the piezoelectric motor according to claim 1;
a drive mechanism driven by the piezoelectric motor; and
a control device controlling the piezoelectric motor.

14. The piezoelectric motor according to claim 1, wherein a length of the fixture portion is longer than a length of the disc spring portion in a radial direction of the rotor.

15. The piezoelectric motor according to claim 7, wherein the sliding member has a plurality of sliding pieces facing each other across a slit, and a bridge connecting the plurality of sliding pieces.

* * * * *